(12) United States Patent
Tash et al.

(10) Patent No.: US 6,309,815 B1
(45) Date of Patent: Oct. 30, 2001

(54) COMPOSITION AND METHOD FOR PREPARATION, STORAGE AND ACTIVATION OF LARGE POPULATIONS OF IMMOTILE SPERM

(75) Inventors: Joseph S. Tash, Leawood; Gerácimo E. Bracho, Overland Park, both of KS (US)

(73) Assignee: University of Kansas Medical Center, Kansas City, KS (US)

(*) Notice: Subject to any disclaimer, the term of this patent is extended or adjusted under 35 U.S.C. 154(b) by 0 days.

(21) Appl. No.: 09/369,559

(22) Filed: Aug. 6, 1999

Related U.S. Application Data

(60) Provisional application No. 60/095,081, filed on Aug. 7, 1998.

(51) Int. Cl.[7] ................................................ A01N 1/02
(52) U.S. Cl. ........................................................... 435/2
(58) Field of Search ............................................. 435/2

(56) References Cited

PUBLICATIONS

Mita, Activation of Respiration in Sea Urchin Spermatozoa by Calcium Ionophore A23187, Comp. Biochem. Physiol. A 77A (4): 689–92 (1984).*

Bibring et al., "Sodium–Dependent pH Regulation in Active Sea Urchin Sperm", Develop. Biology 101 : 425–35 (1984).*

Christen et al., "Ionic Regulation of Sea Urchin Sperm Motility, Metabolism and Fertilizing", J. Physiology 379: 347–65 (1986).*

Bracho et al., "A Method for Preparation, Storage and Activation of Large Populations of Immotile Sea Urchin Sperm", BBRC 237 : 59–62 (1997).*

* cited by examiner

*Primary Examiner*—Sandra E. Saucier
(74) *Attorney, Agent, or Firm*—Sonnenschein Nath & Rosenthal; Lana M. Knedlik

(57) ABSTRACT

A method and composition for extending the viability of immotile sperm is disclosed. The method comprises the steps of (a) preparing an animal for semen collection; (b) collecting semen from the animal; (c) treating the collected semen with a storage buffer solution to substantially inhibit sperm motility; (d) storing the semen for a length of time and at a certain temperature; and (e) reactivating the sperm to normal motility by mixing the inhibited sperm with an activation buffer.

18 Claims, 3 Drawing Sheets

COMPOSITION AND METHOD FOR PREPARATION, STORAGE AND ACTIVATION OF LARGE POPULATIONS OF IMMOTILE SPERM

RELATED APPLICATIONS

This application is based on provisional application Ser. No. 60/095,081 filed Aug. 7, 1998.

FIELD OF INVENTION

This invention relates to the collection, treatment and storage of large quantities of quiescent sperm, and more particularly to a novel method of storing immotile sperm for several days at 4–5° C. without the use of exogenous metabolic inhibitors, antioxidants or detergents.

BACKGROUND OF THE INVENTION

The collection and storage of immotile sperm has been widely studied in sea urchin and avian species. Despite such efforts, storage of viable samples has been limited to short timeframes, e.g. 6–12 hours with turkey sperm. Indeed, extensive efforts have been directed to developing liquid storage procedures for holding turkey sperm for 24 hours and longer (Bakst, et al., Oviductal Sperm Selection, Transport and Storage in Poultry, POULT. SCI. REV., 5:117–43 (1994); Thurston, Storage of Poultry Semen above Freezing for 24–48 Hours, PROC. FIRST INT'L SYMP. ARTIF. INSEM., 107–22 (1995); Bakst, et al., Modification ofEthidium Bromide Exclusion Procedure for Evaluation of Turkey Sperm, POULT. SCI., 70: 336–70 (1991); Lake, Recent Progress in Poultry Reproduction, WORLD'S POULT. SCI. J., 45:53–59 (1989); Wishart, Physiological Changes in Fowl and Turkey Sperinatozoa During in vitro Storage, B R. POULT. SCI., 30:443–454 (1989); Sexton, Comparison of Commercial Diluents for Holding, TurkTey Sperm 24 Hours at 5° C., POULT. SCI., 67:131–34 (1988); Sexton, Research Note: Influence of Damaged Spermatozoa on the Fertility of Turkey Semen Stored for 24 Hours at 5° C.) However, these studies demonstrate that fertility is generally lower when hens are inseminated with semen stored more than 6 hours.

The basic procedures for semen collection and artificial insemination (AI) for poultry was established in the 1930's (Lake, Historical Perspective of Artificial Insemination Technology, FIRST INT'L. SYMP. ARTIF. INSEM. POULT., pp. 1–20 (1995)). Various methods such as refrigeration, cryopreservation, diluents/buffer systems, detergents, antioxidants and exogenous metabolic inhibitors have been utilized to increase storage viability; however, none of these have proved to be unequivocally successful in obtaining the desired effects.

A significant feature of the reproductive physiology of poultry, for example, is the hen's ability to store fertile sperm for long periods of time. Sperm storage tubules, which are structures found in the distal half of the oviduct of all avian species, sequester and store sperm which are slowly released over time to insure an adequate population of sperm at the site of fertilization (Donoghue, A. M., et al., Storage of Poultry Sperm, 1997, unpublished; Bakst, Oviductal Sperm Storage in Poultry: A Review, REPROD. FERTIL. DEV., 5:595–599 (1993)). Turkey hens inseminated before the onset of egg production can produce fertilized eggs up to 16 weeks after insemination (Christensen et al., Efficacy of Fertilization in Artificially Inseminated Turkey Hens, POULT. SCI., 68:724–729 (1989)). The mechanisms of prolonged sperm storage in the sperm storage tubules are unknown, but they are believed to include reversible suppression of sperm respiration and motility as well as stabilization of the plasma membrane and maintenance of the acrosome (Bakst 1993, supra).

There are many diluents in the prior art to extend and maintain sperm viability in vitro. For example, with turkey semen, diluents such as Beltsville Poultry Semen Extender II, Instruments for Veterinary Medicine formula and Minnesota Turkey Growers Association formula have long been used commercially. The basic characteristics common to nearly all diluents include agents to maintain pH, osmolarity and to provide an energy source for sperm (see review, Christensen, Diluents, Dilution and Storage of Poultry Semen for Six Hours, FIRST INT'L. SYMP. ARTIF. INSEM. POULT., pp. 90–106 (1995)). The buffering agents have included mixtures of phosphates, citrates and/or organic zwitterionic molecules such as BES (N,N-bis(2-hydroxyethyl)-2-aminoethanesulfonic acid) and TES (N-Tris(hydroxymethyl)methyl-2-aminoethanesulfonic acid). One phenomenon apparently consistent with the diluents of the prior art is the decline in fertility with poultry semen stored greater than 6 hours after the first 5 to 8 weeks of egg production. Over the course of egg production, the efficiency of the sperm storage tubules decreases and, thus, even late season declines in fertility and hatch are not uncommon with fresh inseminations. When semen is stored 24 hours or longer, in vitro fertility problems are magnified (Donoghue, et al., 1997, supra). Recently, appropriate concentrations of lipid and amphipathic-soluble antioxidants maintained viability, membrane integrity, and motility of turkey sperm after 48 hour in vitro storage better than the control (Donoghue, et al., Effects of Water- and Lipid-Soluble Antioxidants on Turkey Sperm Viability, Membrane Integrity, and Motility During Liquid Storage, POULT. SCI., 76:1440–45 (1997)). However, maintenance of fertility was not established in vivo. Accordingly, there is a definite need to create a diluent/buffering system which mimics the environment for sperm storage within the hen thereby allowing the in vitro storage of semen for extended periods of time without decreasing in vivo fertility.

Additionally, an improved sperm storage system is needed for sea urchin sperm and sperm of other species. With sea urchins, many studies aimed at examining the intracellular signaling pathways that initiate the activation of flagellar motility have relied on detergent-permeabilized sperm reactivated with exogenous $^{32}$P-ATP (Bracho et al., METHODS CELL BIOL. 47:447–458 (1995); Brokaw, J. CELL. BIOCHEM. 35:175–184 (1987)). However, the normal conditions of sperm collection and reactivation allow variable levels of motility to be expressed prior to analysis (Brokaw, ANN. N.Y. ACAD. SCI. 438:132–141 (1984), as well as phosphorylation of many sperm proteins that are not clearly related to flagellar motility (Chaudhry, et al., CELL MOTIL. CYTOSKELETON 32:65–79 (1995); Tash et al., BIOL. REPROD. 28:75–104 (1983)). Thus, identification of the few relevant proteins that are rapidly phosphorylated during the initial stages of sperm activation is difficult. Metabolic inhibitors or extended incubations at cold temperatures prior to reactivation of motility have been used to try and reverse the effects of background motility. See, e.g., Ahmad et al., ARCH. ANDROL. 35:187–208 (1995); Tash, et al., J. CELL BIOL. 103:649–655 (1986); Lindemann, CELL 13:9–18 (1978). However, these methods depend on endogenous enzyme activities that may reverse the signals originally induced in the background motility. Thus, a reliable method of collecting large amounts of immotile sperm capable of normal activation when required would solve this problem.

SUMMARY OF THE INVENTION

It is a principal object of the present invention to provide an improved composition and method for effectively storing immotile sperm without impairing fertility.

Another object of the invention is to provide an improved composition and method for the collection, treatment and storage of immotile sperm obtained from sea urchin species.

A further object of the invention is to provide an improved composition and method for storing immotile sperm without the use of exogenous metabolic inhibitors, antioxidants or detergents.

According to a broad aspect of the invention, there is provided a method for extending the viability of immotile sperm, comprising the steps of: (1) preparing an animal for semen collection; (2) collecting semen from said animal; (3) treating the collected semen with a buffer solution to substantially inhibit sperm motility; (4) storing the treated semen for a length of time and at a certain temperature; and (5) reactivating the sperm to normal motility. The preparation step, an important aspect of the invention, comprises washing the animal by sequential immersion into three trays with cold sperm storage buffer (MSSB) at approximately 5° C. to remove sea water. The animal is bathed in each tray for 30–45 seconds using latex gloves and then placed briefly on paper towels to drain excess buffer.

The objectives, features and advantages of the present invention will become more apparent to those skilled in the art from the following more detailed description of the preferred embodiment of the invention made in conjunction with the accompanying drawings.

DETAILED DESCRIPTION OF THE PREFERRED EMBODIMENTS

Figure 1:
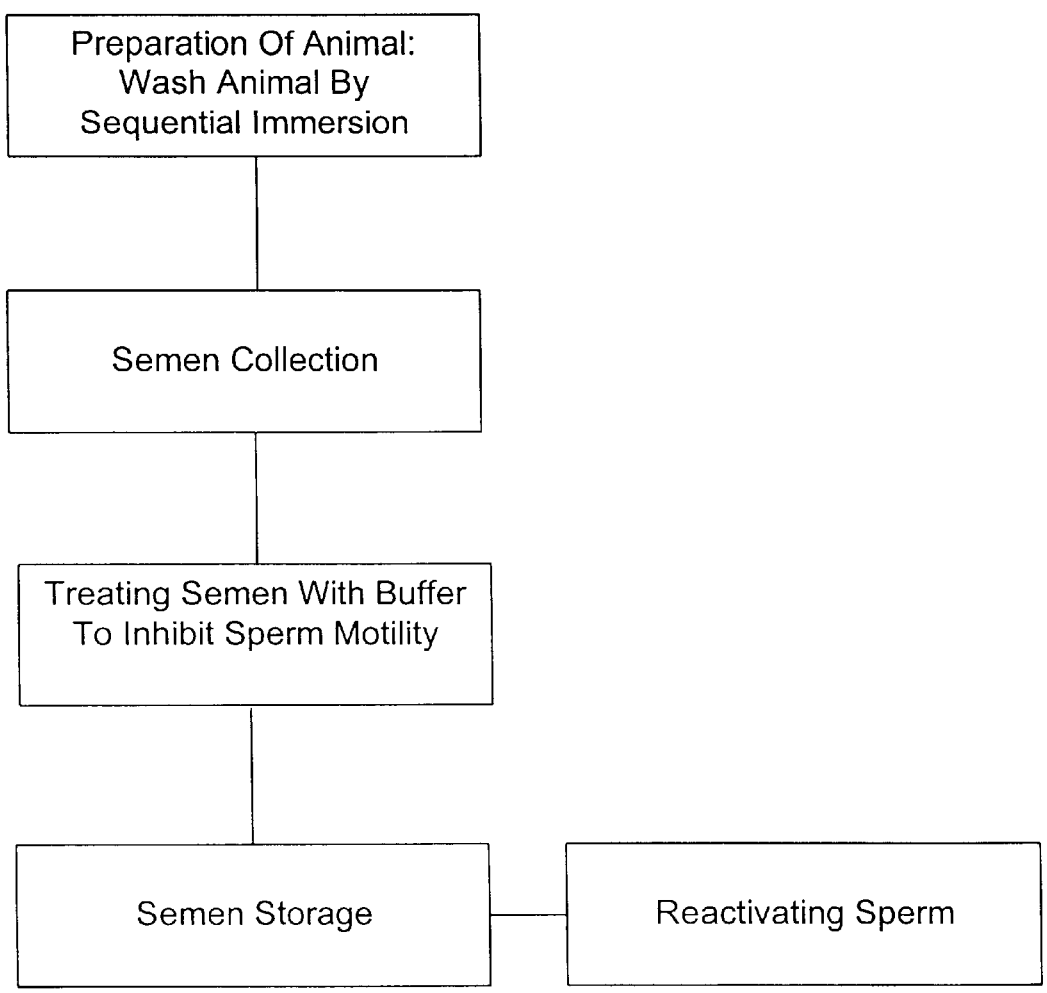
FIG. 1 is a flowchart depicting the inventive process 10 for preparing the animal and collecting, treating and storing immotile sperm.

A flow chart depicting the inventive process 10 for collecting, treating and storing immotile sperm is shown in FIG. 1. As shown in FIG. 1, the present invention generally comprises the steps of preparing the animal, semen collection from the animal, treating the semen with a buffer solution, storing the buffered semen mixture, and reactivating the sperm's motility. Collection can be accomplished by various known methods. In the collection process, it is important that the handler be careful not to contaminate the semen sample with feces, urine or bacteria, which adversely affect semen quality.

The collected semen is diluted with a buffered salt solution to extend the semen, maintain sperm viability in vitro and ultimately maximize the number of animals inseminated. In the inventive process, the following buffers are utilized: artificial sea water (ASW); hardware sea water (HSW); sperm storage buffer (SSB); and 2-[N-morpholino] ethanesulfonic acid (MES) sperm storage buffer (MSSB). The chemical composition of these buffers are:

Composition of Buffers for Collection, Storage and Activation of Immotile Sperm

|  | ASW | HSW | SSB | MSSB |
| --- | --- | --- | --- | --- |
| PH | 8.0 | 8.3 | 6.0 | 6.0 |
| KCl | 10 | 0 | 50 | 50 |
| MES | — | — | — | 5 |
| TAPS | 5 | 5 | 5 | 5 |
| NaCl | 425 | 425 | 425 | 425 |
| $MgCl_2$ | 27 | 27 | 27 | 27 |
| $MgSO_4$ | 29 | 29 | 29 | 29 |
| $CaCl_2$ | 10 | 10 | 10 | 10 |
| $NaHCO_3$ | 2.4 | 2.4 | 2.4 | 2.4 |

Note: All concentrations are given in mM. The symbol "—" means no MES addition; TAPS = 3-[tris-(hydroxymethyl)methylamino]-1-propanesulfonic acid.

Adjustment of HSW to pH 8.3 is necessary to make the final solution pH 8.0 after addition of sperm in SSB or MSSB. In addition, the following buffers are used: Motility assay buffer (MAB) containing 0.1% bovine serum albumin (BSA) or polyvinyl pyrrolidone (PVP) in ASW; and nonmotility assay buffer (NMAB) containing 0.1% BSA in MSSB or SSB. Adding BSA to these buffers prevents sperm from sticking to the plastic surfaces used in motility measurements.

The following example illustrates the present invention.

Example 1—Sea Urchins

Preparation of Sperm

Ripe sea urchins (*Stronglyocentrotus purpuratus* and *Lylechinus pictus*) were obtained from Marinus (Long Beach, Calif.). The animals were washed by sequential immersion into 3 trays containing 2L each of cold sperm storage buffer (SSB) at approximately 5° C. to remove sea water. The animals were bathed in each tray for 30–45 seconds using latex gloves and then placed briefly on paper towels to drain excess buffer. Shedding of gametes was induced by intracoelomic injection of 1–2 ml cold 0.5M KCl throug several sites on the peristomial membrane of the oral side. Sperm were collected by inverting male sea urchins over beakers filled with cold MSSB. Sperm were allowed to settle for 30–40 minutes at 5° C. and then carefully collected with a Pasteur pipette, to avoid resuspension and excessive dilution with buffer. A pool of sperm from several animals was made to minimize individual variations. A few experiments were carried out with sperm from animals that were not washed with SSB prior to spawning. In these instances, sperm were also collected in MSSB as described above. In addition, a portion of sperm was collected directly into ASW for use as a control to assess the activation of motility of sperm collected in MSSB. Storage of sperm was always done at 4–5° C.

Activation and Quantitation of Sperm Motility

Immotile sperm were activated by dilution into activation buffer (HSW) as described below. Control experiments were carried out by transferring sperm into non-activation buffer (MSSB). Quantitative analysis of sperm motility was performed as described below. Adjustments were made to compensate for the greater average curvilinear velocity of sea urchin sperm compared to other species. Motility chambers were prepared by attaching a press-on letter 'O' (Chartpak RDC 49) to the center of a plastic petri dish (Falcon 1029). The 32 um thick letters created a well of fixed depth. Sperm were diluted into HSW for activation, or MSSB for control. The sperm suspension was then immediately diluted into MAB or NMAB. Dilutions were made at a ratio of 1 ul of sperm suspension to 200 ul of MAB or NMAB, to yield approximately 10–30 sperm per field during video microscopy. A 10 ul aliquot of t he diluted sperm was then placed in the center of the well. A plastic cover slip (Fisher 12–547) was then carefully pressed over the suspension using the reverse end of a 5 ml Pipetman pipette tip (Fisher 21-375-3) to seal the chamber and ensure uniform well depth and distribution of the sperm. Motility was quantitated within 2 minutes of sperm dilution. To examine the effect of temperature on motility activation, some experiments were performed with sperm that were allowed to incubate at room temperature in MSSB prior to initial dilution into SSB or MSSB and then subsequent dilution into NMAB for motility analysis. Times of incubation are described where appropriate.

Video microscopy was performed at room temperature (22° C.) using a Nikon Diaphot inverted microscope with 20×BM phase objective and 1× video adapter connected to a Dage CCD72 camera. The video signal was sent via a video time clock (For.A VTG33) to a Panasonic VHS video recorder (Model AG-2550). Motility was recorded on multiple viewing fields for 15 seconds per field for a total of 4 minutes.

Video tapes were analyzed using the CellTracks, version 5.0 (Motion Analysis Corp.). Adjustable parameters were set as follows: frame rate=60/sec; duration of capture=23 frames; minimum motility=25 um/sec; maximum burst speed=700 um/sec; micron/pixel ratio=1.2401; minimum cell size=3 pixels; maximum cell size=12 pixels; number of cells to find per well=400; minimum number of fields per sample=3. Data from a minimum of 400 cells was collected. Replicate wells were analyzed for each treatment. Parameters quantitated were percent motility (MOT), curvilinear velocity (VCL), straight line velocity (VSL), linearity (LIN), amplitude of lateral head displacement (ALH), average path velocity (VAP), and population progressiveness (PRG= MOT×VCL/100). Statistics were calculated from replicate well data.

Previous methods of collection of immotile sperm allow spawning directly on the surface of the animal to avoid contact of the dry sperm with the activation conditions of ASW. In the inventive method, animals were washed in SSB prior to spawning to minimize the risk of sperm contact with the pH and potassium conditions which promote motility activation. In addition, this method yields immotile sperm that do not have to be treated with metabolic inhibitors to reduce background motility.

Results

Figure 2:
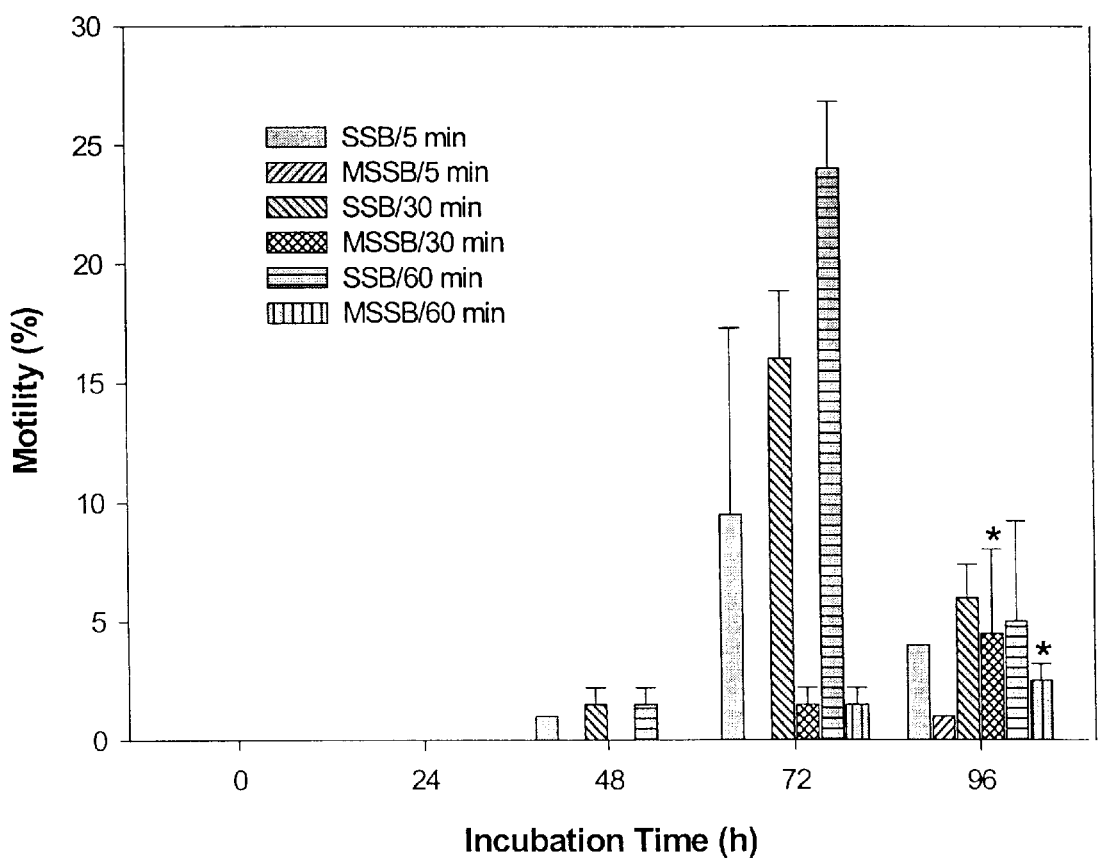
FIG. 2 is a bar graph showing the effect of spawning pre-treatment, storage and incubation conditions on sea urchin sperm motility. The sea urchins were washed in sperm storage buffer (SSB) or MES sperm storage buffer (MSSB) as described below in the detailed description of the preferred embodiment. Sperm stored in SSB and MSSB at 4–5° C. were incubated at room temperature (22° C.) for 5, 30 and 60 minutes prior to an initial dilution in SSB and MSSB and a final dilution in NMAB where motility was quantitated. Bars indicate mean value ± standard deviation. Missing bars indicate 0% motility for all replicates. Statistical comparisons of motility between SSB and MSSB at each 5, 30 and 60 minute time point were all significantly different (P<0.02 or better) except for the 30 and 60 minutes at 96 hours (no significant difference indicated by *).
Figure 3:
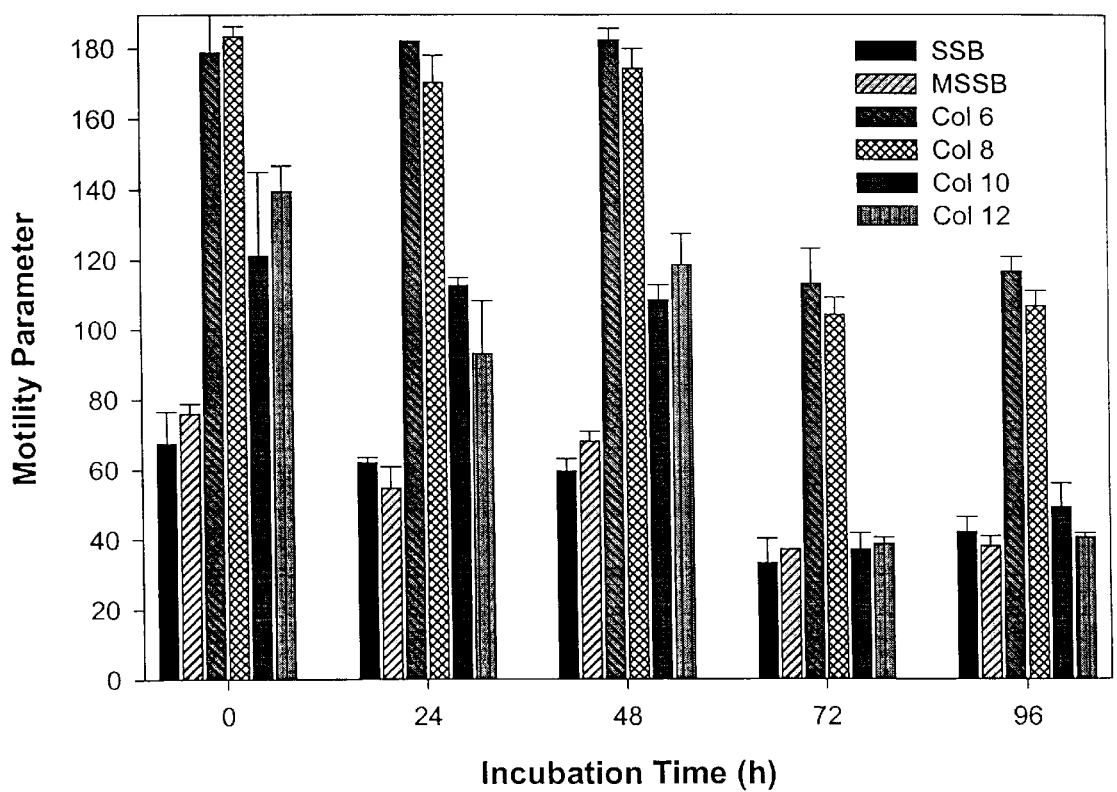
FIG. 3 is a bar graph showing the effect of storage conditions on sperm motile properties. Sea urchins were washed and spawned in SSB or MSSB as described below in the detailed description of the preferred embodiment. Sperm stored in SSB and MSSB at 4–5° C. were activated at 22° C. by an initial dilution in HSW following by a final dilution in MAB where motility was quantitated. Bars indicate mean value ± standard deviation. No significant differences were found in any of the motile properties of activated sperm stored in SSB and MSSB.

Applicants' studies indicate that the buffering capacity of solutions used for collection and storage determine the propensity of sperm to initiate motility activation. This is supported by the results shown in FIG. 2, which indicate that SSB appeared to have enough buffering capacity to prevent sperm activation for the first 24 hours, but was insufficient after 48 hours storage at 4–5° C. FIG. 2 also shows that activation of motility within SSB was enhanced by incubation at room temperature. Sperm activation was significantly higher after 72 hours storage and the effect of incubation at room temperature was also significantly higher. In contrast, no activation was observed in sperm stored in MSSB for 48 hours at 4–5° C. and incubated at room temperature for up to 60 minutes (FIG. 2). After 72 hours storage at 4–5° C., some activation of MSSB sperm was observed but only on sperm incubated for 30 and 60 minutes at room temperature prior to motility analysis. After 96 hours storage at 4–5° C. and 5 minutes incubation at room temperature, sperm stored in SSB showed motility activation that was significantly higher than the motility activation of sperm stored in MSSB. However, activation of sperm motility was similar in both buffers after 30 and 60 minute room temperature incubation. The results presented in FIG. 2 could be attributed to the buffer composition of ASW, HSW, SSB and MSSB. Due to the presence of 5mM TAPS (pKa-8.4 at 25° C.) to SSB, sperm activating buffers (ASW and HSW) had good buffering capacity at pH 8.0 and pH 8.3, and sperm stored in MSSB remained immotile after 48 hours, and essentially remained immotile after 96 hours storage at 4–5° C. No significant differences were found in the motile properties of sperm stored for 96 hours at 4–5° C. in SSB or MSSB after activation by dilution in HSW and MAB, as shown in FIG. 3. It appears, however, that the motility parameters of sperm decreased substantially after 72 hours storage in both buffers. The effect of these storage conditions on the functional properties of sperm, namely fertility, is under investigation.

Additionally, applicants found that increasing the MES concentration in MSSB to 10 mM appears to be toxic to sperm. The activation of immotile sperm stored in MSSB containing 10mM MES was significantly lower when diluted in HSW than similar dilution of sperm stored in SSB or MSSB containing 5 mM MES (data not shown). Applicants found no difference in the activation of sperm collected from animals that were washed with SSB or MSSB prior to spawning.

Applicants did not attempt to determine whether there was a pH change in SSB due to presence of sperm; however, it is postulated that some of the observed activation of sperm in SSB was due in part to a slight increase in pH during storage. Moreover, Applicants observed a significant difference in the pH of SSB and MSSB at low temperature in the absence of sperm. After initial adjustment to pH 6.0 at room temperature, SSB showed an increase of 0.2 pH units after incubation overnight at 5° C., whereas MSSB showed no pH change. Finally, activation could also be due to exposure of sperm to sea water remaining on the surface of the animals during spawning. This is consistent with the finding that fresh sperm from animals that were not washed with SSB prior to spawning exhibited flagellar motility regardless of the buffer used for collection These results were observed in sperm analyzed less than 2 hours after collection and are summarized in the Table below. Applicants found that sperm from these animals showed no significant activation (<0.5% motility) in either buffer when analyzed with no incubation at room temperature. However, after 5 minutes incubation at room temperature, both sperm exhibited activation of motility (percent motility was 5±1.4 in SSB and 2±0.7 in MSSB).

Motility Parameters of Sperm from Animals Not Washed Prior to Spawning

| Parameter | Incubation time (min) | |
|---|---|---|
| | 5 | 50 |
| SSB MOT (%) | 5 ± 1.4 | 17 ± 2.9 |
| MSSB MOT (%) | 2 ± 0.7 | 9 ± 1.3 |
| SSB VCL (um/sec) | 111 ± 7.8 | 282 ± 23.5 |
| MSSB VCL (um/sec) | 220 ± 15.4 | 162 ± 10.5 |
| SSB PRG (um/sec) | 5.6 ± 1.4 | 48 ± 5.6 |
| MSSB PRG (um/sec) | 4.4 ± 1.3 | 15 ± 2.3 |

Note. Incubations were performed at room temperature (22° C.) prior to initial dilution of sperm into SSB or MSSB and subsequent dilution into NMAB for motility quantitation. Numbers indicate mean value ± standard deviation.

activation of motility was considerably higher if incubation at room temperature was extended to 50 min, particularly in sperm collected in SSB (17±2.9 percent motility in SSB versus 9±1.3 in MSSB). These results also support the idea that the buffering capacity at pH 6.0 provided by 5 mM MES plays a key role in the inhibition of motility activation of sperm collected and stored in MSSB. Although the exact mechanism is unknown, inhibition of motility by MSSB appears to be due to the effect of its chemical composition on the internal sperm pH and its high potassium concentration, which is similar to that found in echinoderm testicular luminal fluid. These inhibition conditions are reversed by dilution of sperm into HSW, thus allowing excellent activation.

Applicants have formulated a chemically defined solution that allows preparation, storage and activation of immotile sea urchin sperm for up to 4 days at 4–5° C. with no apparent adverse effects on the motile properties of the activated sperm. Data from these experiments indicate a low background of phosphorylation and that only a few proteins show changes in the degree of phosphorylation during the initial stages of flagellar motility activation. This is in contrast with similar experiments using detergent-permeabilized sperm in which numerous proteins appear to undergo phosphorylation changes during the reactivation process in a high background of phosphorylation.

Although the foregoing invention has been described in some detail by way of example, it will be readily apparent to those of ordinary skill in the art in light of the teachings of this invention that certain changes and modifications may be made thereto without departing from the spirit or scope of the appended claims.

We claim:

1. A method for extending the viability of sperm which has the capacity to become motile comprising the steps of:
   (a) preparing an animal for semen collection by washing the animal with a preparation solution;
   (b) collecting semen from said animal;
   (c) treating the collected semen with a storage buffer solution to inhibit motility by at least 90 percent;
   (d) storing the semen for a length of time and at a certain temperature in said storage buffer solution; and
   (e) reactivating the sperm to normal motility by mixing the inhibited sperm with an activation buffer.

2. The method of claim 1 wherein said preparing comprises washing the animal by immersion into a buffer solution containing 2-[N-morpholino]-ethanesulfonic acid.

3. The method of claim 1 wherein the storage buffer solution comprises a solution containing 2-[N-morpholino]-ethanesulfonic acid.

4. The method of claim 1 wherein sperm storage buffer solution comprises a formulation of 50 mM potassium chloride, 5 mM 2-[N-morpholino]ethanesulfonic acid, 5 mM 3-[tris(hydroxymethyl)methylamino]-1-propanesulfonic acid, 425 mM sodium chloride, 27 mM magnesium chloride, 29 mM magnesium sulfate, 10 mM calcium chloride, and 2.4 mM sodium bicarbonate.

5. The method of claim 1 wherein the stored sperm is reactivated to normal motility by diluting the stored sperm with an activation buffer at a ratio of four parts sperm to seventeen parts activation buffer.

6. The method of claim 5 wherein the activation buffer is hardware sea water.

7. The method of claim 1 wherein said storage is performed in a sperm storage buffer solution having a pH of about 6.0.

8. The method of claim 1 wherein said storage is performed at a temperature of about 4–5° C.

9. The method of claim 8 wherein the semen is incubated at room temperature prior to said storage at about 4–5° C.

10. The method of claim 1 wherein said storage is performed in a storage solution containing NaCl.

11. The method of claim 1 wherein said washing the animal with a preparation solution comprises washing the exterior of the animal with the preparation solution.

12. The method of claim 1 wherein said sperm is stored for 4 days.

13. A method for extending the viability of sperm which has the capacity to become motile comprising the steps of:
   (a) preparing an animal for semen collection;
   (b) collecting semen from said animal;
   (c) treating the collected semen with a storage buffer solution comprising 2-[N-morpholino]-ethanesulfonic acid to inhibit motility by at least 90 percent;
   (d) storing the semen for a length of time and at a certain temperature in said storage buffer solution; and
   (e) reactivating the sperm to normal motility by mixing the inhibited sperm with an activation buffer.

14. The method of claim 13 wherein said storage is performed in a sperm storage buffer solution having a pH of about 6.0.

15. The method of claim 13 wherein said storage is performed at a temperature of 4–5° C.

16. The method of claim 13 wherein said storage is performed in a storage solution containing NaCl.

17. The method of claim 13 wherein said sperm is stored for 4 days.

18. A composition for preserving and extending the viability of immotile sperm having a pH of about 6.0, comprising about:
   (a) 50 mM potassium chloride;
   (b) 5 mM 2-[N-morpholino]ethanesulfonic acid;
   (c) 5 mM 3-[tris(hydroxymethyl)methylamino]-1-propanesulfonic acid;
   (d) 425 mM sodium chloride;
   (e) 27 mM magnesium chloride;
   (f) 29 mM magnesium sulfate;
   (g) 10 mM calcium chloride; and
   (h) 2.4 mM sodium bicarbonate.

* * * * *

UNITED STATES PATENT AND TRADEMARK OFFICE
CERTIFICATE OF CORRECTION

PATENT NO.     : 6,309,815 B1
DATED          : October 30, 2001
INVENTOR(S)    : Tash et al.

It is certified that error appears in the above-identified patent and that said Letters Patent is hereby corrected as shown below:

Column 1,
Line 31, delete "ofEthidium" and insert -- of Ethidium -- therefor.
Line 35, delete "Sperinatozoa" and insert -- Spermatozoa -- therefor.
Line 36, delete "B R." and insert -- BR. -- therefor.
Line 37, delete "Holding," and insert -- Holding -- therefor.
Line 37, delete "TurkTey" and insert -- Turkey -- therefor.

Column 3,
Line 65, in the section title, delete "EMBODIMENTS" and insert
-- EMBODIMENT -- therefor.

Column 4,
Line 58, delete "throug" and insert -- through -- therefor.

Column 5,
Line 20, delete "t he" and insert -- the -- therefor.
Line 40, delete "CellTracks" and insert -- CellTrack/s -- therefor.

Column 6,
Line 60, delete "Collection" and insert -- collection. -- therefor.

Column 7,
Line 19, delete "activation" and insert -- Activation -- therefor.

Column 8,
Line 20, delete "about" between "of" and "4-5º".

Signed and Sealed this

Thirteenth Day of August, 2002

Attest:

Attesting Officer

JAMES E. ROGAN
Director of the United States Patent and Trademark Office